United States Patent [19]

Bowen

[11] Patent Number: 4,578,566

[45] Date of Patent: Mar. 25, 1986

[54] SOFT CONTACT LENS DISINFECTING UNIT

[76] Inventor: John G. Bowen, 1144 The Strand, Manhattan Beach, Calif. 90266

[21] Appl. No.: 738,279

[22] Filed: May 28, 1985

[51] Int. Cl.⁴ .............. H05B 3/06; A61L 2/04
[52] U.S. Cl. ..................... 219/521; 219/386; 219/439; 219/505; 219/541; 422/38; 422/119; 422/307
[58] Field of Search ............... 219/430, 438, 439, 521, 219/386, 214, 385, 328, 401, 433, 441, 504, 505, 541; 422/38, 117, 119, 300, 301, 307, 302; 116/114 U, 116 Y; 338/22 R

[56] References Cited

U.S. PATENT DOCUMENTS

| 3,998,590 | 12/1976 | Glorie et al. | 422/117 |
| 4,178,499 | 12/1979 | Bowen | 219/439 |
| 4,341,948 | 7/1982 | Sundström et al. | 219/521 |
| 4,529,868 | 7/1985 | Bowen et al. | 219/521 |

Primary Examiner—Volodymyr Y. Mayewsky
Attorney, Agent, or Firm—Keith D. Beecher

[57] ABSTRACT

An electrically energized soft contact lens disinfecting unit formed of a surfactant resistant plastic material to render the unit immune from attack by detergents used to clean the lenses prior to placing the lenses in the unit.

2 Claims, 6 Drawing Figures

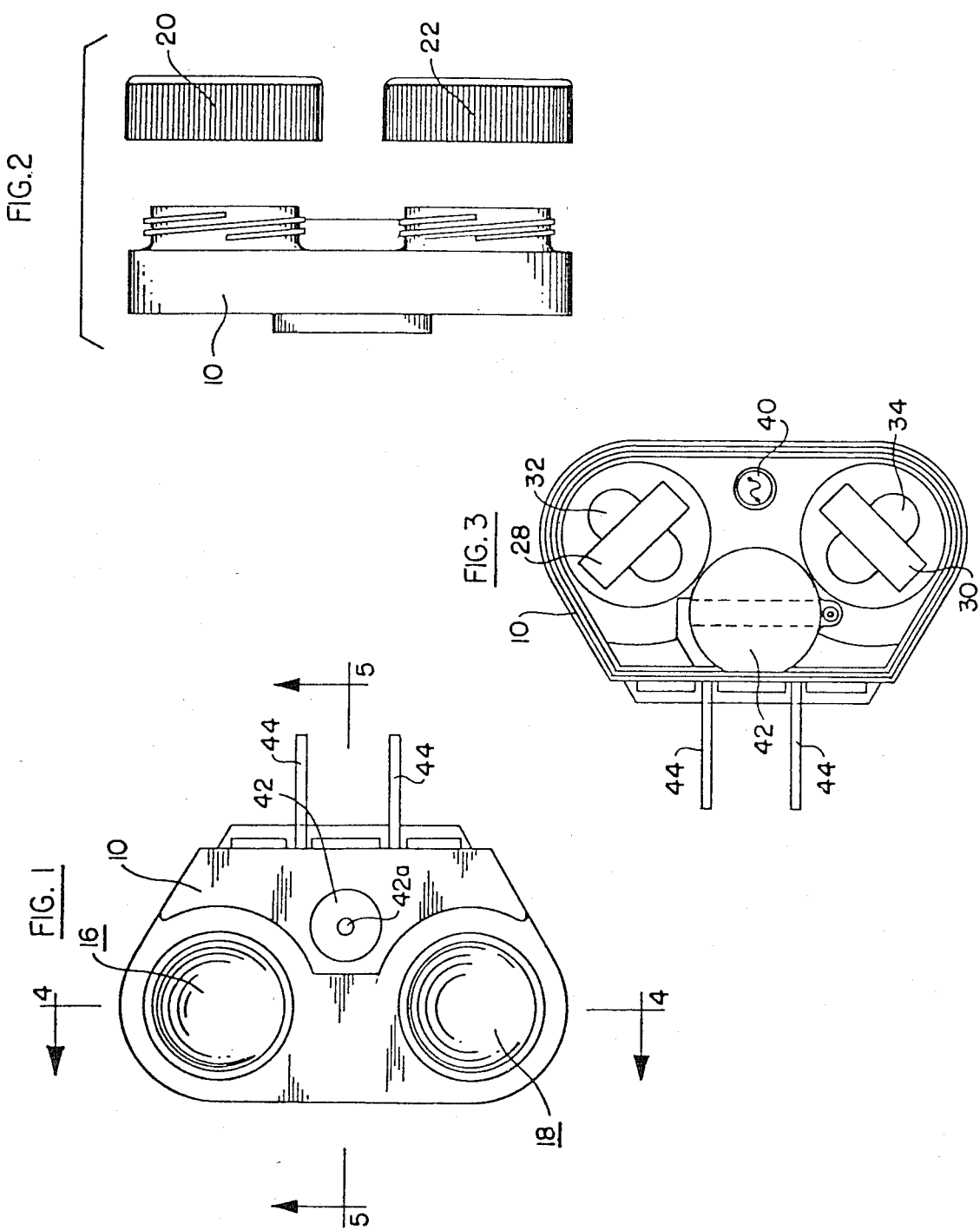

SOFT CONTACT LENS DISINFECTING UNIT

BACKGROUND OF THE INVENTION

An electrically energized soft contact lens disinfecting unit is described and claimed in Copending Application Ser. No. 448,281 which was filed Dec. 9, 1982 in the name of the present inventor and Stephen Hauser, and which issued July 16, 1985 as U.S. Pat. No. 4,529,868 . The unit of the Copending Application will be described herein as an example of a typical soft contact lens disinfecting unit which may incorporate the teachings of the present invention so as to be immune from surfactant contamination.

The Copending Application discloses an electrically energized soft lens disinfecting unit which is compact in size in that the unit itself forms a holder for the lenses having separated compartments for the left and right lenses which are adapted to be filled with an appropriate saline solution, the solution in the compartments being heated by electrical heating elements within the unit to perform the desired disinfecting functions. The unit is equipped with a electric plug which may be directly inserted into an electric receptacle to energize the heating elements.

The soft lens disinfecting unit described in the Copending Application achieved widespread commercial success. However, it was found that some of the units developed leaks after a period of use, and for a long time, the reason for the leaks could not be determined. It was finally found, however, that the leaks were due to contamination of the plastic material from which the unit was formed from certain surfactants used in the manufacture of certain brands of detergents on the market to be used for cleaning soft contact lenses.

Accordingly, the principal objective of the present invention is to provide an electrically energized soft contact lens disinfecting unit which is constructed of a surfactant- resistant plastic material so as to be immune from contamination and resulting leakage regardless of the type of detergent used to clean the lenses to be disinfected by the unit.

As discussed in the Copending Application, previously, hard contact lenses were the only type available, and while such lenses required cleaning, disinfection was not a particular problem. Soft contact lenses, on the other hand, are made from a porous plastic material which absorbs water and, upon doing so, becomes soft and pliable. While hard contact lenses must be cleaned and disinfected on a periodic basis, the soft contact lenses must be disinfected more or less on a daily basis, because the porous nature of the plastic material provides an ideal medium for bacteria.

Accordingly, the soft contact lenses must be cleaned, usually by a detergent sold for the particular purpose, and disinfected in a disinfecting unit on a regular basis, preferably daily. As described above, the present invention has resulted from a finding that some brands of detergent used for cleaning the soft contact lenses cause contamination of the plastic of the disinfecting unit with resulting leakage.

The soft contact lenses may be disinfected by cleaning the lenses with an appropriate detergent, and then by placing the lenses in a saline solution and heating the saline solution to a temperature sufficiently high to destroy any bacteria which might be present in the lenses. One such unit for disinfecting soft contact lenses is described in Copending Application Ser. No. 448,281, as mentioned above. Another type of soft lense disinfecting unit is described in U.S. Pat. No. 4,158,126. The concept of the present invention may be used in conjunction with the soft lens disinfecting units described in the Copending Application and in U.S. Pat. No. 4,158,126, so as to render the unit impervious to surfactant attack, so that the units are capable of long term use without leakage regardless of the brand of detergent used for cleaning the lenses disinfected by the units.

BRIEF DESCRIPTION OF THE DRAWINGS

FIG. 1 is a top plan view of the upper housing of a unit described in Copending Application Ser. No. 448,281, with the covers of the two lens disinfecting compartments of the unit removed;

FIG. 2 is a side view of the upper housing of the unit of FIG. 1, showing the covers displaced up from the top of the upper housing;

FIG. 3 is a bottom view of the upper housing of the unit of FIG. 1 revealing the components mounted within the upper housing;

DETAILED DESCRIPTION OF THE ILLUSTRATED EMBODIMENT

Figure 5:
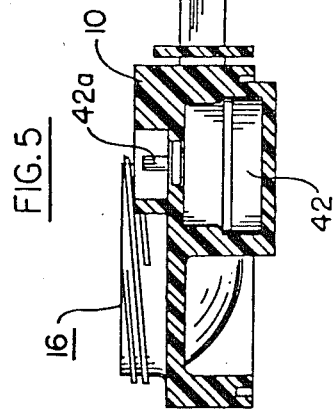
FIG. 5 is a section of the upper housing taken along the line 5—5 of FIG. 1.

The soft lens disinfecting unit illustrated in the drawings includes an upper housing 10 formed of a selected plastic material, and a lower housing 12 (FIG. 4) formed of the same plastic material. As explained above, the plastic material used to form the upper and lower housings is a surfactant resistant plastic. One such plastic, for example, is sold by the Emser Company of N.C. under the trade designation "Grilamid". This plastic is a Nylon 12 derivative.

The upper housing is configured to define a pair of adjacent wells or compartments 16 and 18 each of which is intended to be filled with an appropriate saline solution, so that the left lens may be placed in one of the compartments, and the right lens may be placed in the other. When the lenses are placed in the saline solution in the compartments, covers 20 and 22 (FIG. 2) are screwed down over the tops of the compartments.

Figure 4:
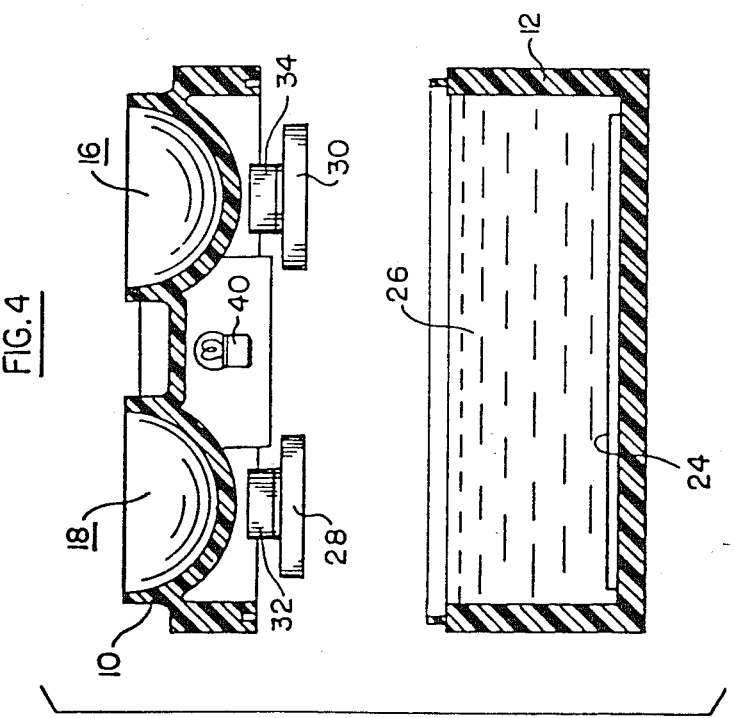
FIG. 4 is a section of the upper housing taken along the line 4—4 of FIG. 1, and also showing the lower housing displaced from the upper housing.

The upper housing 10 is fitted down over the lower housing 12, and the two housings are bonded together. The lower housing is preferably transparent, and a red indicator sheet 24 is affixed to the bottom of the lower housing (FIG. 4). The lower housing is filled with an appropriate material such as paraffin wax 26.

A pair of heating elements 28 and 30 are mounted in the upper housing under the corresponding compartments 16 and 18, and thermal cut-off switches 32 and 34 are mounted on the respective heating elements. The thermal cut-off switch is served to de-energize the unit whenever the temperature at the particular cut-off switch reaches a predetermined threshold level.

A light bulb 40 is also mounted in the upper housing, and it is illuminated when the unit is energized. When the wax 26 is melted, it becomes transparent, so that the bulb 40 causes a red glow to eminate from the bottom of the lower housing 12, due to the red indicator sheet 24, to indicate intervals when the unit is actually energized.

Also, the red indicator sheet is visible through the side walls of the transparent lower housing 12 when the wax is molten, to indicate that the wax is in a molten state.

The unit also includes a switch 42 which has a push-button 42a protruding through the top of the upper housing, as shown in FIG. 1, and the switch is closed when the push-button 42a is depressed. The unit has a pair of electrically conductive blades 44 protruding from one side constituting an electric plug which may be inserted directly into a electric receptacle.

Figure 6:
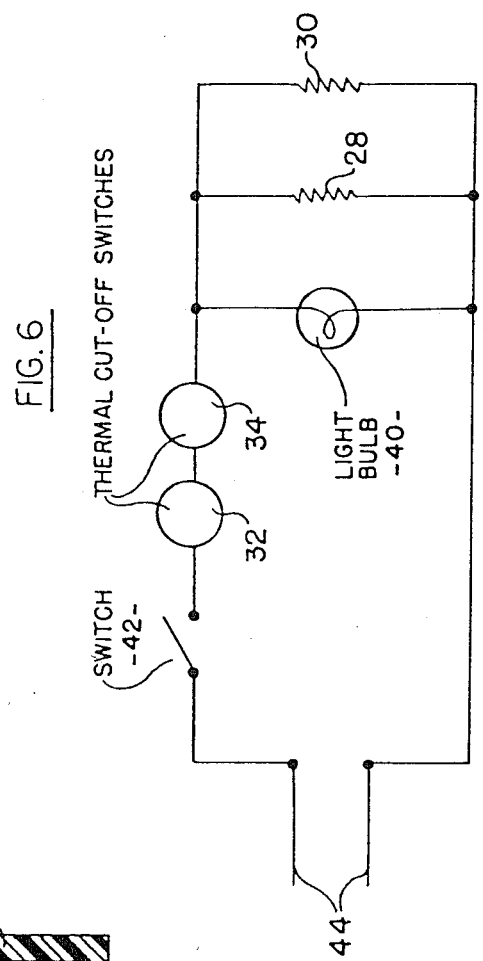
FIG. 6 is a circuit diagram showing the connections to the various electrical elements within the unit.

The various electrical elements of the unit are connected in the manner shown in FIG. 6.

In order to disinfect a pair of soft contact lenses, the electric plug formed by blades 44 is inserted into an electric receptacle, and an appropriate saline solution is placed in the compartments 16 and 18. The soft contact lenses for the left and right eyes are then cleaned by an appropriate detergent and inserted into the compartments, and the covers 20 and 22 are screwed in place. The pushbutton 42a is then depressed to close switch 42, and light bulb 40 is illuminated to indicate that the unit is in an energized state. The heating elements 28 and 30 continue to heat up so long as switch 42 is closed.

When the heating elements 28 and 30 are energized, the wax within the housing becomes liquid, and the red indicator 24 may be viewed through the side wall. A predetermined interval after the indicator becomes visible, switch 42 is opened by again pressing pushbutton 42a, and the unit gradually cools down, with the temperature of the saline solution being sufficient to sterilize the lenses.

Should the temperature of either heating element 28 or 30 rise above a predetermined threshold, the corresponding thermal cut-off switch 32 or 34 operates to deactivate the unit.

As described above, the housing of the unit, in accordance with the invention, is formed of a surfactant resistant plastic material, so that regardless of the type of detergent used to clean the contact lenses prior to their being placed in the compartments 16 and 18, the plastic housing is not susceptible to contamination, and the unit continues to operate on a leak-free basis over long intervals of time.

It will be appreciated that while a particular embodiment of the invention has been described, modifications may be made. It is intended in claims to cover all modifications which come within the spirit and scope of the invention.

I claim:

1. An electrically energized heating unit for disinfecting soft contact lenses, and the like, which are normally cleaned by detergents, comprising: a housing of a plastic material immune from surfactant contamination and resulting leakage regardless of the type of detergent used to clean the lenses disinfected by the unit, and said housing having at least one compartment for receiving the soft contact lenses to be disinfected; electrically energized heating means mounted in the housing adjacent to the compartment; and electric circuitry mounted in the housing for connecting the heater means to an energizing source.

2. The electrically energized heating unit defined in claim 1, in which said plastic comprises a Nylon 12 derivative sold under the trademark "Grilamid".

* * * * *